Figure 1:
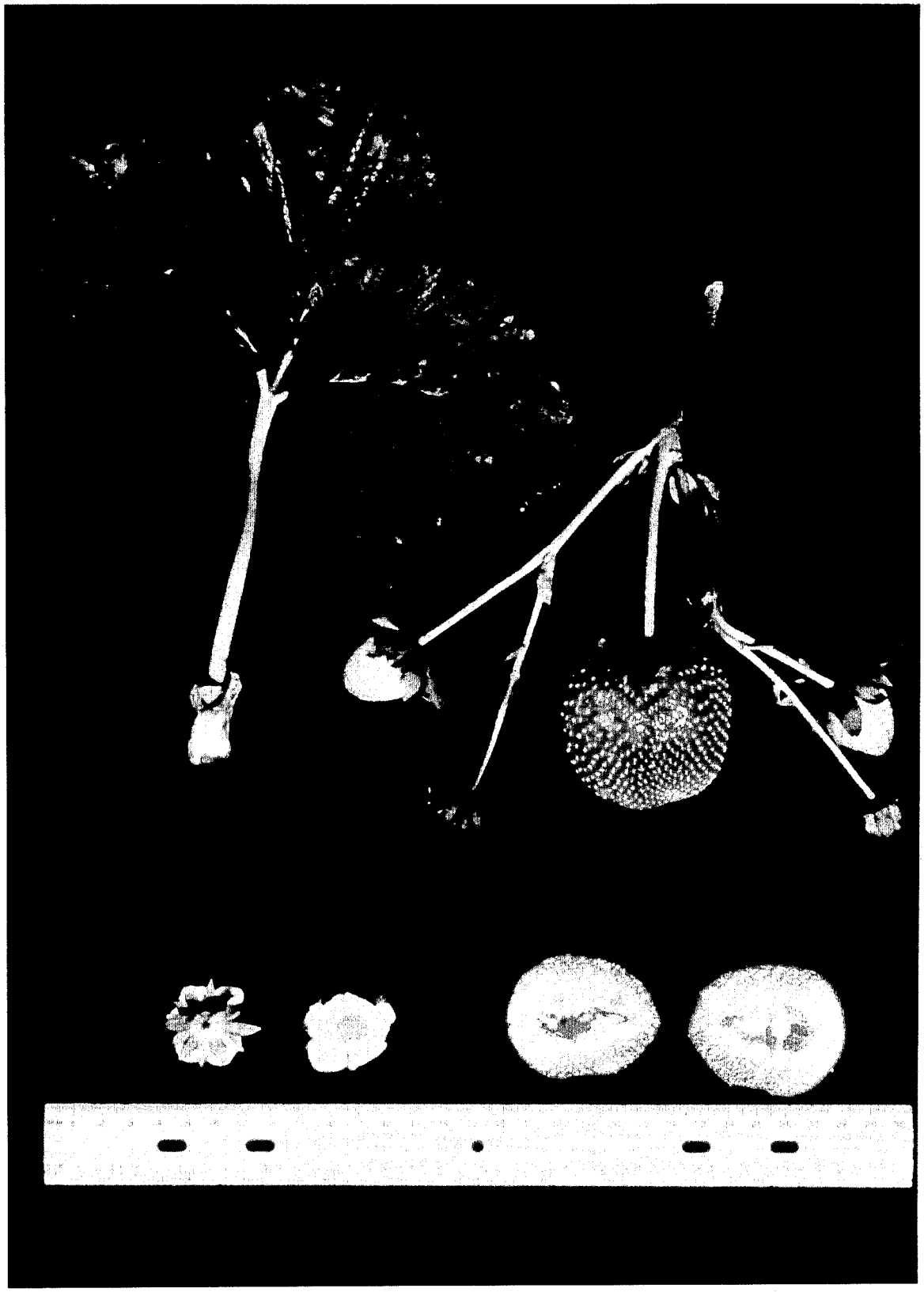

United States Patent [19]

Johnson, Jr. et al.

[11] Patent Number: Plant 7,160

[45] Date of Patent: Feb. 20, 1990

[54] STRAWBERRY PLANT NAMED K1

[75] Inventors: Harold A. Johnson, Jr.; Amado Q. Amorao; Joseph I. Espejo, Jr., all of Watsonville, Calif.

[73] Assignee: Driscoll Strawberry Associates, Inc., Watsonville, Calif.

[21] Appl. No.: 277,071

[22] Filed: Nov. 28, 1988

[51] Int. Cl.[4] ..... A01H 5/00

[52] U.S. Cl. ..... Plt./48

[58] Field of Search ..... Plt./48

*Primary Examiner*—Robert E. Bagwill

*Attorney, Agent, or Firm*—Townsend and Townsend

[57] ABSTRACT

A new and distinct spring bearing variety of strawberry plant, characterized by its ability to produce large attractive primary fruit from the main and subsequent crops that meet the standard required for Driscoll's long stem fruit. These berries are produced if given the chilling necessary before winter planting. This production of large fruit can be produced in mid-summer, as well as during the spring.

The variety is particularly distinguished by its good fruit appearance with yellow seed and a medium to large plant. This plant is considered to have a high degree of susceptibility to mildew and its large attractive fruit is susceptible to shipping injury which influences its shelf life.

1 Drawing Sheet

DESCRIPTION

This invention relates to a new and distinct variety of strawberry plant, named 'K1', which is a cross of the Driscoll patented variety U.S. Plant Pat. No. 4,763 and a Driscoll selection J45.40.

The seedlings resulting from the aforementioned cross were grown and asexually multiplied in Shasta County, Calif., and tested in the fruiting beds on the property of growers of the Driscoll Strawberry Associates, Inc. Clones of the seedlings were also held at the Propagation Nursery in Shasta County. One plant was selected from the aforementioned group of seedlings and further asexually reproduced in the Shasta County nursery of Driscoll Strawberry Associates, Inc. Tests followed in various parts of California during intervening seasons on various properties of grower members of the Driscoll Strawberry Associates, Inc. These tests indicated the merits of 'K1' and resulted in its selection as a promising test variety.

In the drawings:

FIG. 1 illustrates plant parts of the new variety, typical in size, shape and color.

The berry shown in cross section illustrates flesh color and characteristic core cavity. The inflorescence pictured illustrates typical branching and relative size during late May. In this illustration, one ripe berry is present, but it is common for a large secondary berry to ripen at the same time. The pedicel holding the primary berry originates at the axil of two secondary peduncles, but it can also originate from one of the peduncles. Both the pedicel holding the primary berry and the common peduncle are often longer than the ones pictured. The illustration doesn't show a leaflet bract at the axil originating at the common peduncle, but it is often present. The petioles also do not show bracts, but they may be present. The large, dark wedge-shaped berry with yellow exerted seed is typical. The seed at times may be inserted. The illustration shows a secondary and tertiary pedicel fused together. The full exposed calyx is not from a primary berry and is not as large as a calyx from a primary, but the sepals are typical of their outline.

The novel plant of 'K1', which is considered a high chilling spring bearing variety, is usually medium to large and vigorous if given the correct amount of chilling before being planted. The 'K1' is adapted to the central-coastal region of California where the large fruit size during May, June, July and August can reach its potential. This makes this variety adapted to being marketed as a "Long Stem" variety (where the fruit is sold with the pedicel left attached to the calyx). The crown crop as well as the main crop is not as early as the 'Swede' variety (U.S. Plant Pat. No. 6,191). The crown crop is not as consistently uniform in shape or color as 'Swede' and even the main crop of the new variety varies in shape and may be mottled in color. Both the skin and flesh are usually as dark or darker than 'Swede'. 'K1' has the ability to produce large spectacular "Long Stems" with good appearance. It does not, however, have the shelf life of 'Swede', as the skin of larger berries may be injured more easily than that of 'Swede'. It also varies from 'Swede' in that the plant is large if given the same care and winter chilling, and the leaves are larger, but become lighter in color. The inflorescence of the new variety is longer, especially later in the fruiting season. The hair on tertiaries is irregularly parallel to the pedicels in contrast to the hair on 'Swede' which is perpendicular. The fruit of 'K1' is more prone to be wedge-shaped with large round shoulders. The seed of the 'K1' is also more prone to be exerted and remain yellower in color than that of 'Swede'. When comparing the isozymes in leaf extract, the PG1 of the new variety is A4 and 'Swede' is A1.

Both 'Swede' and 'K1' are susceptible to powdery mildew, but 'K1' is even more susceptible. 'K1' has not been tested for its susceptibility to Verticillium wilt and has been found to be susceptible to *Colletotrichum acutatum.* The flavor of 'K1' is considered good, but has not rated as high as 'Swede' in flavor panels.

The varietal characteristics described below in detail were observed mainly during May, June and July in the central coast area of California which is a cool coastal area near the Pacific Ocean. The color terminology is in accordance with the Munsell Color System.

*Plant.*—Medium to large in size as a winter planted variety if given adequate chilling before and after planting. The plant is considered to have a high chilling requirement when grown in the central California coast.

*Leaves.*—Medium to large in size. Bracts may or may not be present on the petioles. Leaflet surface is considered distinctly rugose. Color of leaflets varies from 0.7G 3.4/8.5 to 9.3GY 3.0/6.8 and there may be color variations on a given leaflet. The isozymes in leaf extract is PG1-A4, LAP's B3, and PGM is C2, as designated by R. Bringhurst. This testing was done by Driscoll Strawberry Associates Laboratory following the procedure described in the publication, "Electrophoretic Characterization of California Strawberry Cultivars" by Bringhurst-1981.

*Runners.*—Runners are vigorous and abundant at the nursery, as well as the fruiting bed, even when given the correct chilling for maximum fruit productions.

*Inflorescence.*—Become long in length, especially the common peduncle, as the fruiting season reaches midsummer. The pedicels holding primary berries are usually thick, becoming 2 mm in width, with the length reaching 6 to 7 cm. There are usually two secondary peduncles present, but there may be more late in the fruiting season. The pedicel holding the primary berry may originate from the axil of two secondary peduncles or may originate from one of the peduncles. Secondary berries usually extend farther from the crown than the primary berry. Hair on pedicels 20 mm from the tertiary berry is held irregularly parallel to the pedicel.

*Fruit.*—Crown crop fruit do not become as large as main crop berries. Main crop secondary and tertiary fruit continue to be large. Primaries are quite large, even in August when planted as a winter planted variety and become 40 to 50 mm in length and width. The shape is usually medium wedge in outline as described in the U.S.A. Bulletin 1043. The shoulders are rounded, not necked, with the calyx usually clasping to slightly reflexed. The fruit surface is smooth with a minimum of shallow longitudinal furrows. The fruit surface may be slightly mottled. The fruit is firm, but injures easily and has to be picked with care. The color of the fruit surface is mostly 5.7R 3.8/15.5 and the flesh varies from 5.7R 3.8/15.5 to 60R 3.1/12.0 when the fruit is picked for the fresh market. The seed are held exerted from the fruit surface and remain conspicuously yellow.

*Calyx.*—Large in diameter with those of primary fruit 40 to 45 mm. Individual sepals are ovate to eliptical with acute apexes. Some overlap and some serrations may be present. Color of sepals facing fruit varies from 1.5G 2.8/7.4 to 8.7GY 5.7/12.3.

We claim:

1. The new and distinct variety of strawberry plant herein described and illustrated, and identified by the characteristics enumerated above.

* * * * *